United States Patent [19]

Liepmann et al.

[11] 4,177,287

[45] Dec. 4, 1979

[54] PHARMACEUTICAL COMPOSITIONS OF $N_1$-ACYL-$N_2$-PHENYLDIAMINO-PROPANOLS AND PROCESS FOR THEIR PREPARATION

[75] Inventors: Hans Liepmann; Rolf Hueschens, both of Hanover; Wolfgang Milkowski, Burgdorf; Horst Zeugner; Henning Heinemann, both of Hanover; Klaus-Ullrich Wolf, Haenigsen; Insa Hell; Reinhard Hempel, both of Hanover, all of Fed. Rep. of Germany

[73] Assignee: Kali-Chemie Pharma GmbH, Hanover, Fed. Rep. of Germany

[21] Appl. No.: 900,973

[22] Filed: Apr. 28, 1978

[30] Foreign Application Priority Data

May 10, 1977 [DE] Fed. Rep. of Germany ....... 2720908

[51] Int. Cl.² .................... A61K 31/34; A61K 31/165
[52] U.S. Cl. .................................... 424/285; 424/324
[58] Field of Search ................................ 424/324, 285

[56] References Cited

U.S. PATENT DOCUMENTS 3,998,809   12/1976   Milkowski et al. .............. 260/326 N

*Primary Examiner*—Frederick E. Waddell
*Attorney, Agent, or Firm*—Schwartz, Jeffery, Schwaab, Mack, Blumenthal & Koch

[57] ABSTRACT

Pharmaceutical compositions are disclosed, which are effective in the treatment and prophylaxis of ulcers and which comprise as a pharmacologically active ulcus-inhibiting ingredient a compound selected from the group of $N_1$-acyl-$N_2$-(4-chlorophenyl)-1,3-diaminopropan-2-ols, having the formula I

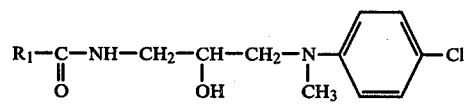

wherein $R_1$ represents 3,4-dimethoxyphenyl, 2-fluorophenyl, 2-trifluoromethylphenyl, or furyl, and pharmaceutically acceptable acid addition salts thereof, and a pharmaceutically acceptable diluent.

Further disclosed is a new process for the preparation of the compounds of formula I.

16 Claims, No Drawings

PHARMACEUTICAL COMPOSITIONS OF N₁-ACYL-N₂-PHENYLDIAMINOPROPANOLS AND PROCESS FOR THEIR PREPARATION

BACKGROUND OF THE INVENTION

The present invention relates to pharmaceutical compositions which are useful in the treatment of ulcers and which comprise $N_1$-acyl-$N_2$-methyl-$N_2$-(4-chlorophenyl)-1,3-diaminopropan-2-ols of formula I

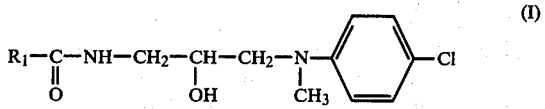

wherein $R_1$ is 3,4-dimethoxyphenyl, 2-fluorophenyl, 2-trifluoromethylphenyl, or furyl, and pharmaceutically acceptable acid addition salts thereof as pharmacologically active ingredients.

These $N_1$-acyl-$N_2$-methyl-$N_2$-(4-chlorophenyl)-1,3-diaminopropan-2-ols have been disclosed in the U.S. Pat. No. 3,998,809. U.S. Pat. No. 3,998,809 discloses that these compounds are valuable intermediates for the preparation of benzodiazepine- and benzodiazocine derivatives which are pharmacologically effective in influencing the central nervous system and which due to these properties are useful as tranquilizers, sedatives, or anticonvulsive agents. Yet, no independent pharmacological activity of the intermediate $N_1$-acyl-$N_2$methyl-$N_2$-(4-chlorophenyl)-1,3-diaminopropan-2-ols has been disclosed.

It is well known in the medical art that the etiology of ulcer formation is very complex. Pharmaceuticals which so far have been used in the treatment of ulcers each influence only partial aspects of these multiple events. Therefore, only limited therapeutical success could be obtained (see Blum, Schweiz. Med. Wochenschrift, 106 (1976) p. 1457).

According to Demling (see L. Demling, Klin. Gastroenterologie I, (1973), p. 202), the balance between the various aggressive and defensive factors which act on the mucous membrane is disturbed in the case of ulcer formation in the stomach and intestines. A therapeutical treatment therefore has to be directed towards redressing this balance.

The conventionally used therapeutic methods were directed towards reducing the aggressive agents (hydrochloric acid, pepsin).

Anticholinergic agents, as for example atropine, have not succeeded in ulcer therapy, because of their side effects which occur already at low dosages. Antiacidic agents do not have a healing effect. Their therapeutical effect is limited only to a pain-reducing component which, with regard to ulcus duodeni, is doubted according to recent experiments (see Blum). Derivatives of glycyrrhetinic acid are known to have a therapeutic effect on ulcers. Yet, serious side-effects, such as aldosterone-like effects, causing a loss of potassium and sodium- and water-retention, strongly limit the possibility of a wider utilization of these derivatives. Psychopharmacological agents have not succeeded in the treatment of ulcers due to a lack of activity. Furthermore, their effects on the central nervous system, such as sedation and influence of motility, are undesirable in ambulatory treatment.

SUMMARY OF THE INVENTION

It is an object of the present invention to provide pharmaceutical compositions which are effective in the treatment of ulcers, in particular peptic ulcers, in larger mammals, in particular human beings. It is a further object of this invention to provide such pharmaceutical compositions which exhibit a direct ulcer-inhibiting activity. It is a further object of the present invention to provide such pharmaceutical compositions, which are low in side-effects and toxicity and exhibit a large therapeutic index.

It is a further object of the present invention to provide such pharmaceutical compositions, which do not substantially influence the secretion in the stomach.

It is a further object of the present invention to provide such pharmaceutical compositions which promote the redressing of the disturbed physiological balance at the mucous membrane and the regeneration of the imparied mucous membrane.

It is a further object of the present invention to provide a method of treatment of physiological disorders which are connected with the formation of ulcers, in particular a method for treatment of peptic ulcers.

It is a further object of the present invention to provide a process for preparing pharmacologically active compounds which are effective in preventing and/or healing ulcers.

In order to accomplish the foregoing objects according to the present invention, there is provided a pharmaceutical composition comprising an ulcus-inhibiting effective amount of at least one compound selected from the group of $N_1$-acyl-$N_2$-methyl-$N_2$-(4-chlorophenyl)-1,3-diaminopropan-2-ols, having the formula I

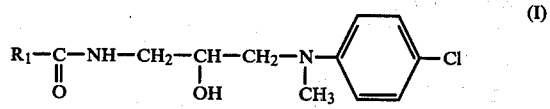

wherein $R_1$ represents 3,4-dimethoxyphenyl, 2-fluorophenyl, 2-trifluoromethylphenyl, or furyl, and pharmaceutically acceptable acid addition salts thereof, and a pharmaceutically acceptable diluent.

According to the present invention, there is further provided a method of treating disorders which are connected with the formation of ulcers, in particular peptic ulcers, in larger mammals, in particular human beings, which comprises the step of administering the above described pharmaceutical composition.

According to the present invention, there is further provided a process for preparing the compounds of formula I in good yields.

Further objects, features, and advantages of the present invention will become apparent from the detailed description of the invention, which follows.

DETAILED DESCRIPTION OF THE INVENTION

It has been found that the compounds
(1) $N_1$-(3,4-dimethoxybenzoyl)-$N_2$-methyl-$N_2$-(4-chlorophenyl)-1,3-diaminopropan-2-ol,
(2) $N_1$-(2-fluorobenzoyl)-$N_2$-methyl-$N_2$-(4-chlorophenyl)-1,3-diaminopropan-2-ol,
(3) $N_1$-(2-trifluoromethylbenzoyl)-$N_2$-methyl-$N_2$-(4-chlorophenyl)-1,3-diaminopropan-2-ol, (4) $N_1$-(2-furoyl)-$N_2$-methyl-$N_2$-(4-chlorophenyl)-1,3-diaminopropan-2-ol possess a therapeutic effect in the treatment of ulcers and disorders which are connected with formation of ulcers, without influencing the acid secretion in the stomach or the central nervous system.

The foregoing compounds of formula I exhibit an outstanding direct ulcer-inhibitory activity combined with a favorably large therapeutic index, without influencing the secretion in the stomach. Therefore, they lead to a redressing of the physiological imbalance at the mucous membrane which has been disturbed due to the illness. Furthermore, they are low in side-effects and toxicity.

Description of the Pharmacological Test Methods

1. Acute toxicity

The acute 7-day-toxicity is determined after a single application per os in white NMRI-mice which had not been fed. The calculation of the $LD_{50}$ is carried out by probitanalysis by means of electronic data processing (see L. Cavalli-Sforza, Gustav Fischer-Verlag, Stuttgart (1964), Grundbegriffe der Biometrie, pp. 153).

2. Effectiveness against indomethacine-induced ulcers in the rat (Modified test procedure according to U. Jahn and R. W. Adrian, Arzneimittel Forschung, (Drug Res.) 19, (1969), p. 36).

To at least 6 male rats, having a body-weight of from 170 to 220 g, dosages of the test compounds are administered orally in an amount of 0.5 ml of a suspension medium per 100 g animal body-weight. The animals of the blank control group received the corresponding amount by volume of the suspension medium only. One hour after application of the test compounds, a dosage of 20 mg per kg of indomethacine contained in an amount of 0.5 ml of a suspension per 100 g animal body-weight, are orally applied to each animal for producing ulcers. 24 hours after the application of indomethacine, the animals are sacrificed.

The evaluation of the results is effected according to a modification of the method according to O. Muenchow, (Arzneim. Forsch. (Drug Res.)4, (1954) pp. 341-344). The mean value and the standard deviation of the numbers of ulcers is calculated and subsequently the inhibiting activity of the test compounds and a standard compound are calculated as percent inhibition compared with the blank control group.

3. Effect on the secretion in the stomach of narcotized rats (determination of the pH-value)

For evaluating the effect of the test compounds on the secretion in the stomach, a modification of the procedure according to M. N. Ghosh and H. O. Schild (Brit. J. Pharmacol. 13, (1958) p. 54) is used. The test is performed on narcotized (urethane narcosis) male rats, having a body weight of from 200-230 g. For this purpose N/4000-sodium hydroxide solution is perfused into the stomachs of rats at a rate of 1 ml per minute by means of a cardia- and pylorus-catheter. The pH value of the perfusate, which leaves the stomach by way of the pylorus catheter, is determined by means of a one-rod measuring system, and is continuously registered.

In order to perform a comparative control test, after a pre-run period of 20 minutes, 10 mg per kg of acetylcholine are applied intraperitoneously. The resulting comparative control value is defined as being 100.

After the starting value has been reached again, the test compound is applied intraduodeneously.

For evaluation, the surface-integral is calculated numerically with the aid of the rule of Simpson. The degree of inhibition of the secretion is calculated from the difference between the surfaces before and after the application of the test compound.

The above listed $N_1$-acyl-$N_2$-methyl-$N_2$-(4-chlorophenyl)-1,3-diaminopropan-2-ol-compounds numbers 1 through 4 have been tested according to the above described methods. The following have been used as standard control substances:

A. atropine sulfate
B. licorice extract.

The results are shown in Table 1 below. From the data in Table 1 it is apparent that the ulcus-inhibiting agents according to the present invention exhibit a good ulcer-inhibiting activity without inhibiting the secretion in the stomach.

TABLE 1

| Compound No. | Toxicity $LD_{50}$ p.o. (mg/kg) | Inhibition of indomethacine induced ulcers | | Inhibition of secretion in the stomach | |
|---|---|---|---|---|---|
| | | dosage p.o. (mg/kg) | % inhibition | dosage p.o. (mg/kg) | % inhibition |
| 1 | >6810 | 68 | 44 | 300 | 0 |
| 2 | >1470 | 68 | 49 | 300 | 0 |
| 3 | >1470 | 75 | 40 | 300 | 0 |
| 4 | >1470 | 68 | 44 | 300 | 0 |
| A | 721 | 12 | 26 | 0.5 i.p.* | 100 |
| B | >10000 | 150 | 13 | 300 | 0 |

*)At a low dosage already, atropine causes a strong inhibition of the secretion in the stomach, yet at this point does not have a sufficiently strong effect on the ulcer. Higher dosages are not advisable due to the well known side-effects.

Due to their above mentioned pharmacological properties, the $N_1$-acyl-$N_2$-methyl-$N_2$-(4-chlorophenyl)-1,3-diaminopropan-2-ols of formula I and their pharmaceutically acceptable acid addition salts, are useful in medical treatment, in particular in the treatment and prophylaxis of ulcers, in particular peptic ulcers, and physiological disorders which favor the formation of such ulcers. Pharmaceutically acceptable non-toxic acid addition salts of the compounds of formula I can be prepared in conventional manner by reacting the free base of formula I with an appropriate acid. Suitable acids are, e.g., mineral acids, such as sulfuric acid, hydrochloric acid, hydrobromic acid, or orthophosphoric acid, or organic acids, such as, e.g., malonic acid, succinic acid, fumaric acid, maleinic acid, p-toluenesulfonic acid, or cyclohexylaminosulfonic acid. The acid addition salts of the compounds of formula I can be pharmaceutically used in the same manner as the free base of formula I.

According to a feature of the invention, there are provided pharmaceutical compositions containing at least one of the compounds of formula I or their pharmaceutically acceptable salts. The compositions may take the form of solid or liquid formulations for enteral, preferably oral, or for parenteral administration. Thus, the pharmaceutical formulations may be in solid form, e.g., in the form of capsules, tablets, coated tablets, or suppositories, or in liquid form, e.g., in the form of solutions, suspensions, or emulsions. These formulations may comprise conventional inorganic and/or organic inert pharmaceutical carriers and adjuvants, which are suitable for enteral and/or parenteral administration. Thus, the pharmaceutical diluents may comprise solids and/or liquid carrier materials, such as, e.g., lactose, starch, gum arabic, gelatin, vegetable oils, fats, polyethylene glycols, and the like. If desired, the pharmaceutical compositions according to the present invention, may further comprise conventional additives, such as preserving agents, stabilizing agents, moisturizers, emulsifying agents, or salts, which serve for regulating the osmotic pressure or as a buffer.

Suitable carrier materials and adjuvants are well known in the pharmaceutical art and are disclosed and/or recommended as adjuvants in the pharmaceutical and cosmetic art and related arts, in the following publications, the disclosure of which is hereby incorporated by reference:

Ullmanns Encyclopedia der technischen Chemie, Vol. 4, (1953), p. 1; Journal of Pharmaceutical Sciences, Vol. 52, (1963), p. 918; Dr. H. P. Fiedler, Lexikon der Hilfsstoffe fuer Pharmazie, Kosmetik and angrenzende Gebiete, Cantor KG. Aulendorf i. Wuertt. 1971.

The pharmaceutical formulations according to the present invention are prepared in any conventional manner, e.g., by dissolving the pharmacologically active agents in at least a portion of liquid carrier materials or by thoroughly mixing the pharmacologically active agents with at least a portion of the solid carrier materials, adding the remaining adjuvants and/or carrier materials, and formulating the resulting mixtures into the desired dosage form by known pharmaceutical methods, e.g., tabletting, molding into suppositories, or filling into capsules. In addition to the $N_1$-acyl-$N_2$-methyl-$N_2$-(4-chlorophenyl)-1,3-diaminopropan-2-ols of formula I, additional therapeutically active ingredients may optionally be included into the pharmaceutical formulations according to the present invention.

In the pharmaceutical compositions, according to the present invention, the amount of the pharmacologically active compound of formula I per single dosage unit may vary according to the type of the compound and the conditions to be treated. In pharmaceutical compositions for oral administration to adult humans, the amount of the compound of formula I per single dosage preferably is in the range of from about 50 to about 150 mg per single dosage form.

The amount of compounds of formula I which suitably is applied for the treatment and prophylaxis of ulcers may of course vary according to the conditions to be treated and the mode of application. For oral application to adult persons, daily dosages of from about 150–450 mg are suitable.

The following non-limiting examples are intended to illustrate the preparation of pharmaceutical compositions according to the present invention.

EXAMPLE 1: Capsules

Capsules containing 100 mg of $N_1$-(3,4-dimethoxybenzoyl)-$N_2$-methyl-$N_2$-(4-chlorophenyl)-1,3-diaminopropan-2-ol as a pharmacologically active ingredient are prepared.
Composition per capsule:

| | |
|---|---|
| pharmacologically active agent | 100 mg |
| lactose | 90 mg |
| highly dispersed silicic acid (commercial product Aerosil 200, manufacturer Degussa) | 4 mg |
| talcum | 4 mg |
| magnesium stearate | 2 mg |
| | 200 mg |

Preparation: The pharmacologically active ingredient is thoroughly mixed with the adjuvants and the mixture is filled into capsules size #2.

The other above mentioned $N_1$-acyl-$N_2$-methyl-$N_2$-(4-chlorophenyl)-1,3-diaminopropan-2-ols and their pharmaceutically acceptable acid addition salts, can be formulated into capsules containing 100 mg of the pharmacologically active agent, by mixing the same with the above-cited adjuvants and filling the resulting mixtures into capsules size #2.

EXAMPLE 2: Tablets

Tablets containing 100 mg of $N_1$-(3,4-dimethoxybenzoyl)-$N_2$-methyl-$N_2$-(4-chlorophenyl)-1,3-diaminopropan-2-ol as a pharmacologically active agent are prepared.
Composition per tablet:

| | |
|---|---|
| pharmacologically active agent | 100 mg |
| lactose | 60 mg |
| corn starch | 30 mg |
| carboxymethylcellulose (commercial product Primojel, manufacturer Scholtens Chemische Fabricken N.V.) | 4 mg |
| gelatin | 2 mg |
| highly dispersed silicic acid (commercial product Aerosil 200, manufacturer Degussa) | 2 mg |
| magnesium stearate | 2 mg |
| | 200 mg |

Preparation: A 10% mucilage of gelatin in water is prepared. The pharmacologically active agent, lactose, corn starch, and carboxymethylcellulose, are mixed, the mixture is then mixed with the mucilage and granulated through a sieve of 1.5 mm mesh-size. The granulate is dried at 40° C., once more passed through the sieve, mixed with the highly dispersed silicic acid, and the magnesium stearate and the mixture pressed into tablets using a die having a diameter of 9 mm.

The other compounds of formula I can be tabletted in the same manner.

EXAMPLE 3: Coated Tablets

Coated tablets, containing 100 mg of $N_1$-(2-fluorobenzoyl)-$N_2$-methyl-$N_2$-(4-chlorophenyl)-1,3-diaminopropan-2-ol as a pharmacologically active ingredient, are prepared.

According to the procedure described in Example 2, tablets containing $N_1$-(2-fluorobenzoyl)-$N_2$-methyl-$N_2$-(4-chlorophenyl)-1,3-diaminopropan-2-ol are prepared and subsequently are coated in a conventional manner. The resulting coated tablets are polished with the aid of beeswax.

A process for the preparation of compounds of formula I has been disclosed in the above mentioned U.S. Pat. No. 3,998,809 and the German Offenlegungsschrift Nos. 2,221,558 and 2,314,993. According to this prior art method, $N_1$-methyl-$N_1$-(4-chlorophenyl)-1,3-diaminopropan-2-ol, is reacted with the appropriate carboxylic acid derivative, having the formula $R_1$—COX, wherein $R_1$ is as defined above and X represents, for example, halogen or lower alkoxy.

According to the present invention, there is provided a new process, by which the compounds of formula I are prepared in good yields. This process comprises the step of reacting an acylamino compound having the formula II

  (II)

wherein R₁ is as defined in claim 1, and Z represents a

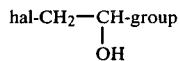

wherein hal is halogen, or Z is the

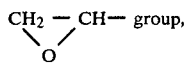

with an aniline compound having the formula

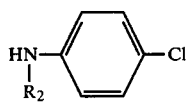  (III)

wherein R₂ is hydrogen or methyl, at a reaction temperature of between about 15° and about 150° C., whereby a reaction mixture containing the 1-acylamino-3-phenylaminopropan-2-ol of formula Ia

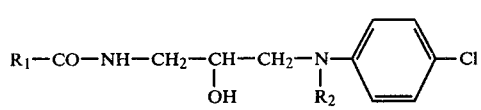  (Ia)

wherein R₁ and R₂ are as defined above is formed.

If in the compound of formula III R₂ is hydrogen, the resulting compound of formula Ia is further methylated to form a compound of formula I.

The compounds of formula I can be recovered in free form or in form of an acid addition salt. If desired, the obtained free base can be reacted with inorganic or organic acids in a conventional manner to form the corresponding acid addition salt thereof. The resulting acid addition salts of compounds of formula I can be transferred into the free base in conventional manner.

The process according to the present invention suitably is carried out in the presence of an additional solvent. The following are examples of suitable solvents: ether, dioxane, tetrahydrofurane, benzene, toluene, xylene, sulfolane, dimethylformamide, dimethylsulfoxide, hexamethylphosphoric acid, and glacial acetic acid.

If a compound of formula II is used, wherein Z represents the group

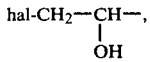

the halogen preferably is chlorine or bromine and the reaction is preferably carried out at a temperature of between about 15° and about 60° C. in the presence of an acid-binding agent, such as, e.g., potassium carbonate, sodium carbonate, sodium hydroxide, or potassium hydroxide.

If in the compounds of formula II, Z represents an ethylenepoxy group, the reaction of this expoxide of formula II with 4-chloro-N-methylaniline or 4-chloroaniline can suitably be carried out at the reflux temperature of the solvent. Yet, the reaction can also be carried out in the presence of a catalyst. Thus, e.g., the reaction can be carried out in the presence of glacial acetic acid.

If 4-chloroaniline is used, the methyl group has to be subsequently introduced into the resulting compound in a conventional methylation procedure. The methylation can be performed by conventional methods which are known from prior art literature, e.g., the reaction with formaldehyde under reducing conditions by the method according to Leuckart-Wallach or by the method according to Eschweiler-Clarke (see H. Krauch W. Kunz, Reaktionen der organischen Chemie (1976), p. 131) or by methylation with dimethylsulfate (see Houben-Weyl,XI/I, (1957), p. 207).

Starting materials of formula II, wherein Z represents a group

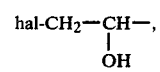

can for example be obtained by reacting 2-phenyl-5-chloromethyloxazolidine with a corresponding aromatic or heterocyclic carboxylic acid chloride of the formula R₁—COCl, wherein R₁ is as defined above, in a conventional method (H. E. Carter et al., J. Amer. Chem. Soc. 75, p. 2503 (1955) M. Bergmann et al., Chem. Ber. 54, p. 1645 (1921).

Starting materials of formula II, wherein Z represents ethylenepoxy, can be prepared according to the methods disclosed in Houben-Weyl, Methoden der Org. Chemie, 6/3, p. 374 (1965), by treating the corresponding 1,2-halogenhydrines of formula II with a strongly basic agent, e.g., pulverized sodium- or potassium hydroxide in an inert solvent, such as ether, dioxane, tetrahydrofurane, benzene, or toluene, at room temperature or elevated temperature. The resulting epoxides of formula II can be further reacted in the process according to the present invention without any prior purification.

The following non-limiting examples further illustrate the preparation of the compounds of formula I.

EXAMPLE 1

At a temperature of −40° C., a solution of 15.2 g 3,4-dimethoxybenzoyl chloride in 40 ml of chloroform is added dropwise to a solution of 15.0 g of 2-phenyl-5-chloromethyloxazolidine in a mixture of 200 ml of chloroform and 6 ml of pyridine. The mixture is heated to room temperature. After a reaction period of 14 hours, 20 ml of concentrated hydrochloric acid are added, the phases are thoroughly mixed for 10 minutes, and then separated. The separated aqueous phase is diluted with water to twice its volume and is saturated with sodium chloride. Then it is extracted with chloroform. After drying the chloroform extract and evaporating the solvent, 15.0 g of N-(3,4-dimethoxybenzoyl)-3-chloro-1-aminopropan-2-ol is obtained as an oil which can be used in the following reaction without any prior purification. After crystallization from ethanol/toluene, the compound melts at 104°–106° C.

9.0 g of the foregoing compound and 4.2 g of 4-chloroaniline are added to a mixture of 2.0 g of finely pulverized potassium hydroxyde in 180 ml of dioxane. After agitating the mixture for 14 hours at room temperature, the reaction mixture is filtered, the solvent is evaporated from the filtrate under vacuum, and the resulting residue is re-dissolved in chloroform. After washing the chloroform phase with water, drying and evaporating the solvent, 7.4 g of $N_1$-(3,4-dimethoxybenzoyl)-$N_2$-(4-chlorophenyl)-1,3-diaminopropan-2-ol are obtained as an oily residue which is crystallized from acetone. Melting point 168°–170° C.

A mixture of 3.6 g of $N_1$-(3,4-dimethoxybenzoyl)-$N_2$-(4-chlorophenyl)-1,3-diaminopropan-2-ol, 19 ml of formic acid and 9.5 ml of 36% aqueous formaldehyde solution is heated on a waterbath for 3 hours. Subsequently, ice is added to the reaction mixture and the mixture is rendered alkaline by adding diluted sodium hydroxide solution, and is extracted with chloroform. The compound is then isolated from the chloroform extract. 2,3 g of $N_1$-(3,4-dimethoxybenzoyl)-$N_2$-methyl-$N_2$-(4-chlorophenyl)-1,3-diaminpropan-2-ol, having a melting point of 118°–121° C., are crystallized from ethylacetate.

EXAMPLE 2

A mixture of 10.5 g of N-(3,4-dimethoxybenzoyl)-3-chloro-1-aminopropan-2-ol in 750 ml of benzene and 2.4 g of finely pulverized potassium hydroxide is agitated at room temperature for a period of 16 hours. The mixture is then filtered and the solvent is evaporated from the filtrate under vacuum. After crystallization from toluene, 7.5 g of N-(3,4-dimethoxybenzoyl)-2,3-epoxy-1-aminopropane, having a melting point of 108°–111° C., is obtained.

A mixture of 2.4 g of the foregoing epoxide, 1.5 g of 4-chloro-N-methylaniline and 0.7 g of acetic acid is heated to a temperature of 60° C. for a period of 6 hours. Subsequently the reaction mixture is dissolved in chloroform, washed with water, dried over sodium sulfate, and filtered. After evaporating the solvent, $N_1$-(3,4-dimethoxybenzoyl)-$N_2$-methyl-$N_2$-(4-chlorophenyl)-1,3-diaminopropan-2-ol is obtained as an oily substance. After crystallization from acetone/petrolether, 2.1 g of the crystalline compound, having a melting point of 118°–121° C., are obtained.

EXAMPLE 3

4.7 g of N-(3,4-dimethoxybenzoyl)-2,3-epoxy-1-aminopropane are reacted with 1.4 g of acetic acid and 2.6 g of 4-chloroaniline, and the reaction mixture is worked up according to the procedure described in Example 2.

After crystallization from acetone, 5.5 g of $N_1$-(3,4-dimethoxybenzoyl)-$N_2$-(4-chlorophenyl)-1,3-diaminopropan-2-ol, having a melting point of 168°–170° C., are obtained.

3.6 g of $N_1$-(3,4-dimethoxybenzoyl)-$N_2$-(4-chlorophenyl)-1,3-diaminopropan-2-ol are dissolved in 35 ml of dioxane. A mixture of 3.0 g of sodium bicarbonate in 6 ml of water is added and subsequently 3.3 ml of dimethylsulfate are added and the mixture is heated to a temperature of 60°–70° C. for a period of 30 minutes. Subsequently, 10 ml of a 15% sodium hydroxide solution are added to the reaction mixture under stirring, the solvent is evaporated under vacuum, the mixture is extracted with chloroform, and the compound is isolated from the chloroform extract. 2.4 g of $N_1$-(3,4-dimethoxybenzoyl)-$N_2$-methyl-$N_2$-(4-chlorophenyl)-1,3-diaminopropan-2-ol, having a melting point of 118°–121° C., are obtained.

EXAMPLE 4

2-chloromethyl-5-phenyloxazolidine is reacted with 2-fluorobenzoyl chloride according to the procedure described in Example 1, whereby N-(2-fluorobenzoyl)-3-chloro-1-aminopropan-2-ol, having a melting point of 77°–78° C., is obtained.

3.3 g of the above described compound are reacted with 0.9 g of potassium hydroxide according to the procedure described in Example 2, whereby N-(2-fluorobenzoyl)-2,3-epoxy-1-aminopropane is obtained. Without any further purification, the resulting oily compound is mixed with 60 ml of toluene and 2.2 g of N-methyl-4-chloroaniline and the mixture heated under reflux for a period of 6 hours. After evaporating the solvent under vacuum and treating the oily residue with petrolether, 2.2 g of $N_1$-(2-fluorobenzoyl)-$N_2$-methyl-$N_2$-(4-chlorophenyl)-1,3-diaminopropan-2-ol, having a melting point of 105°–107° C., are obtained.

EXAMPLE 5

According to the method described in Example 4, N-(2-trifluoromethylbenzoyl)-3-chloro-1-aminopropanol, having a melting point of 79°–81° C., is obtained by reacting 2-chloromethyl-5-phenyloxazolidine with 2-trifluoromethylbenzoyl chloride, subsequently is transformed into N-(2-trifluoromethylbenzoyl)-2,3-epoxy-1-aminopropane by reaction with potassium hydroxide, and the latter is further reacted with 4-chloro-N-methylaniline, whereby $N_1$-(2-trifluoromethylbenzoyl)-$N_2$-methyl-$N_2$-(4-chlorophenyl)-1,3-diaminopropan-2-ol, having a melting point of 107°–109° C., is obtained. The yield in the last reaction step is 44%.

EXAMPLE 6

According to the method described in Example 4, 2-chloromethyl-5-phenyloxazolidine is reacted with 2-furanecarboxylic acid chloride. N-furoyl-3-chloro-1-aminopropan-2-ol, having a melting point of 73°–74° C., is obtained. Subsequently, a mixture of 10.2 g of this compound in 150 ml of tetrahydrofurane and 3.3 g of potassium hydroxide is agitated at room temperature for a period of 14 hours. Without any further purification, the resulting oily N-(2-furoyl)-2,3-epoxy-1-aminopropane is reacted with 6.4 g of 4-chloroaniline and 3.0 ml of glacial acetic acid and the reaction mixture is worked up. Upon trituration with ether, 5.4 g of $N_1$-(2-furoyl)-$N_2$-(4-chlorophenyl)-1,3-diaminopropan-2-ol, having a melting point of 125°–127° C., are crystallized from the raw oil.

A mixture of 4.1 g of $N_1$-(2-furoyl)-$N_2$-(4-chlorophenyl)-1,3-diaminopropan-2-ol, 27 ml of formic acid and 13.5 ml of 36% formaldehyde solution is heated on a waterbath for a period of 3.5 hours. Then the reaction mixture is poured onto ice and is worked up, as described in Example 1. After crystallization from acetone/petrolether, 2.8 g of crystalline $N_1$-(2-furoyl)$N_2$-methyl-$N_2$-(4-chlorophenyl)-1,3-diaminopropan-2-ol, having a melting point of 106°–107° C., are obtained.

What is claimed is:

1. A pharmaceutical composition in dosage-unit-form for oral administration comprising an ulcus-inhibiting effective amount of from about 50 to about 150 mg per single dosage-unit of at least one pharmacologically active compound selected from the group of $N_1$-acyl-$N_2$-(4-chlorophenyl)-1,3-diaminopropan-2-ols, having the formula

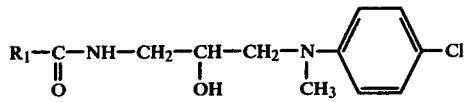

wherein R₁ represents 3,4-dimethoxyphenyl, 2-fluorophenyl, 2-trifluoromethylphenyl, or furyl, and pharmaceutically acceptable acid addition salts thereof, and a pharmaceutically acceptable diluent.

2. The pharmaceutical composition as defined in claim 1, wherein the compound of formula I is $N_1$-(3,4-dimethoxybenzoyl)-$N_2$-methyl-$N_2$-(4-chlorophenyl)-1,3-diaminopropan-2-ol.

3. The pharmaceutical composition as defined in claim 1, wherein the compound of formula I is $N_1$-(2-fluorobenzoyl)-$N_2$-methyl-$N_2$-(4-chlorophenyl)-1,3-diaminopropan-2-ol.

4. The pharmaceutical composition as defined in claim 1, wherein the compound of formula I is $N_1$-(2-trifluoromethylbenzoyl)-$N_2$-methyl-$N_2$-(4-chlorophenyl)-1,3-diaminopropan-2-ol.

5. The pharmaceutical composition as defined in claim 1, wherein the compound of formula I is $N_1$-(2-furoyl)-$N_2$-methyl-$N_2$-(4-chlorophenyl)-1,3-diaminopropan-2-ol.

6. The pharmaceutical composition as defined in claim 1, which is an orally applicable composition.

7. The pharmaceutical composition as defined in claim 6, which is a solid composition.

8. The composition as defined in claim 1, wherein the pharmaceutically acceptable diluent comprises a solid carrier material.

9. The composition as defined in claim 1, wherein the pharmaceutically acceptable diluent comprises a carrier material selected from the group consisting of lactose, starch, gum arabic, gelatin, vegetable oils, fats, and polyethylene glycols.

10. A method of treating peptic ulcers in larger mammals which comprises the step of administerting to a larger mammal an ulcer-inhibiting effective amount of at least one pharmacologically active compound as defined in claim 1, selected from the group of $N_1$-acyl-$N_2$-(4-chlorophenyl)-1,3-diaminopropan-2-ols, having the formula I

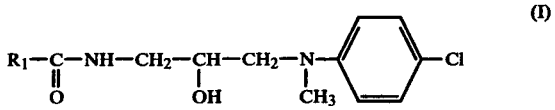

wherein R₁ represents 3,4-dimethoxyphenyl, 2-fluorophenyl, 2-trifluoromethylphenyl, or furyl, and pharmaceutically acceptable acid addition salts thereof, and a pharmaceutically acceptable diluent.

11. The method as defined in claim 10, wherein the compound of formula I is $N_1$-(3,4-dimethoxybenzoyl)-$N_2$-methyl-$N_2$-(4-chlorophenyl)-1,3-diaminopropan-2-ol.

12. The method as defined in claim 10, wherein the compound of formula I is $N_1$-(2-fluorobenzoyl)-$N_2$-methyl-$N_2$-(4-chlorophenyl)-1,3-diaminopropan-2-ol.

13. The method as defined in claim 10, wherein the compound of formula I is $N_1$-(2-trifluoromethylbenzoyl)-$N_2$-methyl-$N_2$-(4-chlorophenyl)-1,3-diaminopropan-2-ol.

14. The method as defined in claim 10, wherein the compound of formula I is $N_1$-(2-furoyl)-$N_2$-methyl-$N_2$-(4-chlorophenyl)-1,3-diaminopropan-2-ol.

15. The method as defined in claim 10, wherein the pharmacologically active compound is administered orally.

16. The method as defined in claim 10, wherein the amount of the pharmacologically active compound is from about 150 to about 450 mg per day.

* * * * *